(12) United States Patent
Wieser et al.

(10) Patent No.: US 8,008,490 B2
(45) Date of Patent: Aug. 30, 2011

(54) POLYMORPHIC FORMS OF ARIPIPRAZOLE AND METHOD

(75) Inventors: Josef Wieser, Polling (AT); Hannes Lengauer, Kundl (AT); Doris Braun, Dornbirn (AT); Ulrich Griesser, Axams (AT); Richard Tessadri, Innsbruck (AT)

(73) Assignee: Sandoz AG, Basel (CH)

( * ) Notice: Subject to any disclaimer, the term of this patent is extended or adjusted under 35 U.S.C. 154(b) by 898 days.

(21) Appl. No.: 11/795,909

(22) PCT Filed: Jan. 27, 2006

(86) PCT No.: PCT/EP2006/000725
§ 371 (c)(1),
(2), (4) Date: Jul. 24, 2007

(87) PCT Pub. No.: WO2006/079548
PCT Pub. Date: Aug. 3, 2006

(65) Prior Publication Data
US 2008/0132518 A1    Jun. 5, 2008

(30) Foreign Application Priority Data
Jan. 27, 2005  (EP) ..................................... 05001638

(51) Int. Cl.
*C07D 401/12* (2006.01)
(52) U.S. Cl. ....................................................... 544/363
(58) Field of Classification Search ................... 544/363
See application file for complete search history.

(56) References Cited

U.S. PATENT DOCUMENTS

| 5,006,528 A | 4/1991 | Oshiro |
| 2004/0058935 A1 | 3/2004 | Bando et al. |
| 2005/0009990 A1 | 1/2005 | Knoll |

FOREIGN PATENT DOCUMENTS

| WO | WO2004/099152 | 11/2004 |
| WO | WO2006/030446 | 3/2006 |

*Primary Examiner* — James O Wilson
*Assistant Examiner* — Ebenezer O Sackey
(74) *Attorney, Agent, or Firm* — Luedeka, Neely & Graham, P.C.

(57) ABSTRACT

The present invention relates to novel polymorphic forms of aripiprazole and processes for producing them. It further relates to pharmaceutical compositions comprising the novel forms and to the use of the novel forms in the treatment of schizophrenia.

13 Claims, 10 Drawing Sheets

POLYMORPHIC FORMS OF ARIPIPRAZOLE AND METHOD

This application is the National Stage of International Application No. PCT/EP/2006/000725, filed on Jan. 27, 2006, which claims benefit under 35 U.S.C. §119 (e) of EP 05001638.5, filed on Jan. 27, 2005, the contents of both are incorporated herein by reference in their entirety.

FIELD OF THE INVENTION

The present invention relates to novel polymorphic forms of aripiprazole and processes for their production. It further relates to pharmaceutical compositions comprising the novel forms and to the use of the novel forms in the treatment of schizophrenia.

BACKGROUND OF THE INVENTION

Aripiprazole, 7-[4-[4-(2,3-dichlorophenyl)-1-piperazinyl]butoxy]-3,4-dihydro-2(1H)-quinolinone, is an antipsychotic drug useful in the treatment of schizophrenia (Merck Index, monograph number 00791, CAS registry number 129722-12-9).

Synthesis and isolation of aripiprazole are described in EP 367141 B1 and U.S. Pat. No. 5,006,528. Additional crystalline anhydrous or hydrous forms are disclosed in WO 03/026659 (conventional hydrate, hydrate A, conventional anhydrate, anhydrate B, anhydrate C, anhydrate D, anhydrate E, anhydrate F, anhydrate G).

Nevertheless, there remains a need for alternative polymorphic forms of aripiprazole which have properties suitable for pharmaceutical processing on a commercial scale. The present invention satisfies these needs by providing novel polymorphic forms of aripiprazole and processes for their production.

SUMMARY OF THE INVENTION

The present invention relates to form X of aripiprazole characterized by an X-ray powder diffraction pattern with peaks at 10.0, 11.6, 15.7, 16.3, 18.5, 20.4, 21.8, 22.2 and 23.3 degrees 2θ.

The present invention further relates to aripiprazole ethanol hemisolvate characterized by an X-ray powder diffraction pattern with peaks at 17.4, 18.1, 19.6, 23.3 and 27.9 degrees 2θ.

The present invention also relates to aripiprazole methanol solvate characterized by an X-ray powder diffraction pattern with peaks at 11.5, 17.3, 18.5, 19.8, 23.1, 24.4 and 26.9 degrees 2θ.

The present invention provides a process for preparing form X of aripiprazole, comprising the steps of:
a) dissolving aripiprazole in a suitable solvent by heating
b) slowly cooling the solution to room temperature or below to effect crystallization
c) optionally isolating crystalline form X of aripiprazole.

The present invention also provides a process for preparing form X of aripiprazole characterized in that a suspension of aripiprazole in a suitable solvent is seeded with crystals of form X and the suspension is stirred at a suitable temperature in order to effect transformation of the used form of aripiprazole into form X.

In another aspect the invention provides a process for preparing aripiprazole ethanol hemisolvate, comprising the steps of:
a) dissolving aripiprazole in ethanol by heating
b) slowly cooling the solution to room temperature or below to effect crystallization
c) isolating the crystalline ethanol hemisolvate
d) drying the ethanol hemisolvate at a temperature below about 60° C.

In a further aspect the invention provides a process for preparing aripiprazole ethanol hemisolvate, comprising the steps of:
a) dissolving aripiprazole in a solvent in which aripiprazole is soluble at room temperature
b) diluting the solution with ethanol
c) isolating the crystalline ethanol hemisolvate
d) drying the ethanol hemisolvate at a temperature below about 60° C.

In a further aspect the invention provides a process for preparing aripiprazole ethanol hemisolvate characterized in that a suspension of aripiprazole in ethanol is stirred at a suitable temperature in order to effect transformation of the used form of aripiprazole into aripiprazole ethanol hemisolvate.

In another aspect the invention provides a process for preparing aripiprazole methanol solvate, comprising the steps of:
a) dissolving aripiprazole in methanol by heating
b) slowly cooling the solution to room temperature or below to effect crystallization
c) isolating the crystalline methanol solvate
d) drying the methanol solvate at a temperature below about 60° C.

In a further aspect the invention provides a process for preparing aripiprazole methanol solvate, comprising the steps of:
a) dissolving aripiprazole in a solvent in which aripiprazole is soluble at room temperature
b) diluting the solution with methanol
c) isolating the crystalline methanol solvate
d) drying the methanol solvate at a temperature below about 60° C.

In a further aspect the invention provides a process for preparing aripiprazole methanol solvate characterized in that a suspension of aripiprazole in methanol is stirred at a suitable temperature in order to effect transformation of the used form of aripiprazole into aripiprazole methanol solvate.

The present invention also relates to form X of aripiprazole or aripiprazole ethanol hemisolvate for use as a medicament.

In another aspect the present invention relates to the use of form X of aripiprazole or aripiprazole ethanol hemisolvate for the preparation of a medicament for the treatment of schizophrenia.

In a further aspect the present invention relates to a pharmaceutical composition comprising an effective amount of form X of aripiprazole or aripiprazole ethanol hemisolvate and a pharmaceutically acceptable carrier.

Other objects, features, advantages and aspects of the present invention will become apparent to those of skill from the following description. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and from reading the other parts of the present disclosure.

DETAILED DESCRIPTION OF THE INVENTION

As used herein the term "crude" refers to crystals of aripiprazole that have not been washed and/or recrystallized to remove impurities that may be present.

As used herein the term "crystalline" refers to crystals of aripiprazole that have been washed and recrystallized to remove impurities.

As used herein the term "amorphous" relates to solid material which lacks a regular crystalline structure.

The term "room temperature" as used herein indicates that the applied temperature is not critical and that no exact temperature value has to be kept. Usually, "room temperature" is understood to mean temperatures of about 15° C. to about 25° C. (see e.g. EU Pharmacopeia 5.0, page 6).

The inventors of the present invention have identified novel polymorphs of aripiprazole. The novel polymorphs have distinct physical properties and may be characterized e.g. by a typical X-ray powder diffraction pattern, infrared spectrum or a characteristic thermogravimetric (TGA) and differential scanning calorimetric (DSC) curve. Each of these characteristics on its own is sufficient to unambiguously define and identify the new polymorphs but they also may be combined with each other.

The present invention relates to a novel form X of aripiprazole characterized by an X-ray powder diffraction pattern with peaks at 10.0, 11.6, 15.7, 16.3, 18.5, 20.4, 21.8, 22.2 and 23.3 degrees 2θ (2-theta).

Figure 4:
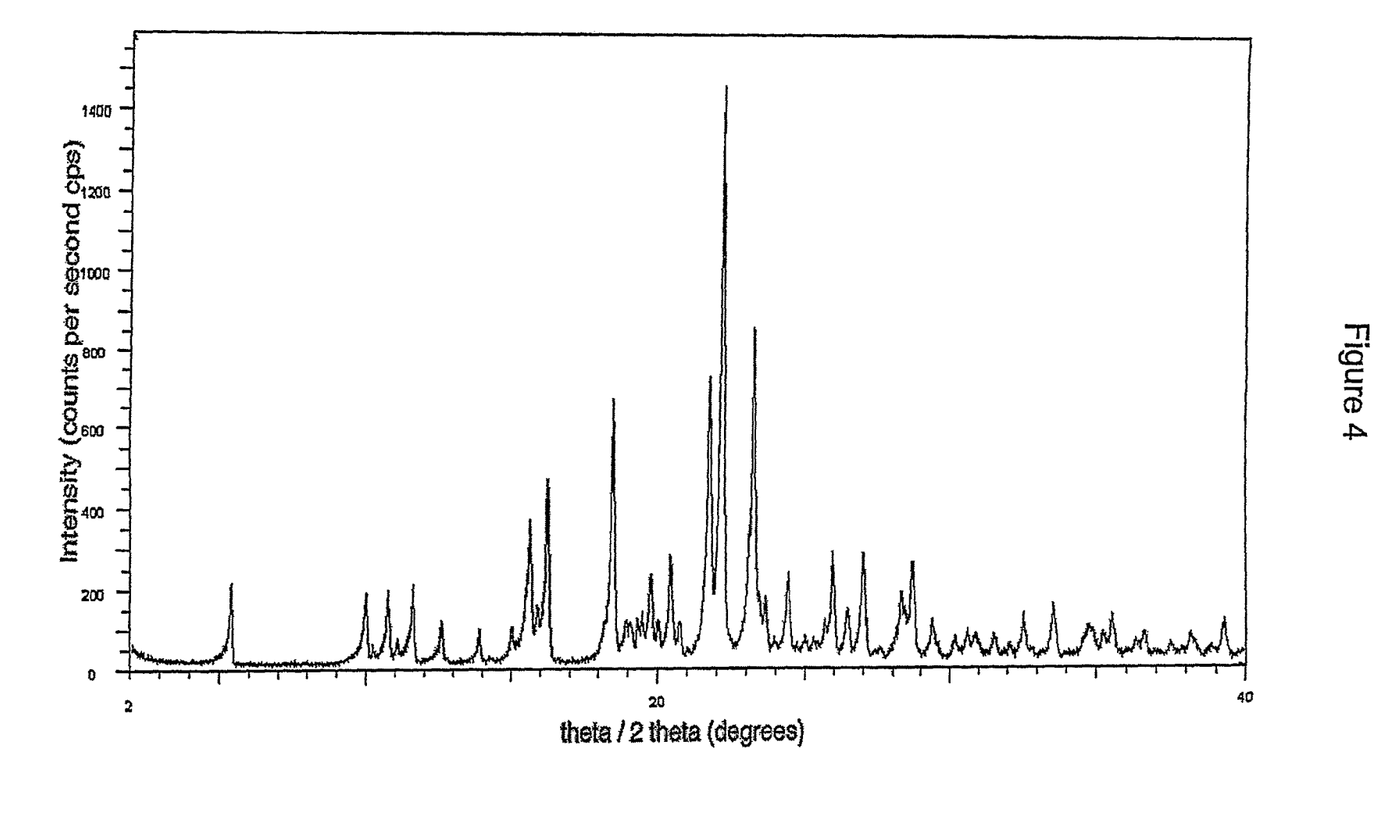
FIG. 4: X-ray powder diffraction pattern of form X of aripiprazole.

A characteristic X-ray powder diffraction pattern of form X of aripiprazole is shown in FIG. 4 and some characteristic peaks are listed in Table 1. Accordingly, in a preferred embodiment, the present invention relates to a novel form X of aripiprazole characterized by an X-ray powder diffraction pattern substantially in accordance with Table 1 and FIG. 4.

Figure 1:
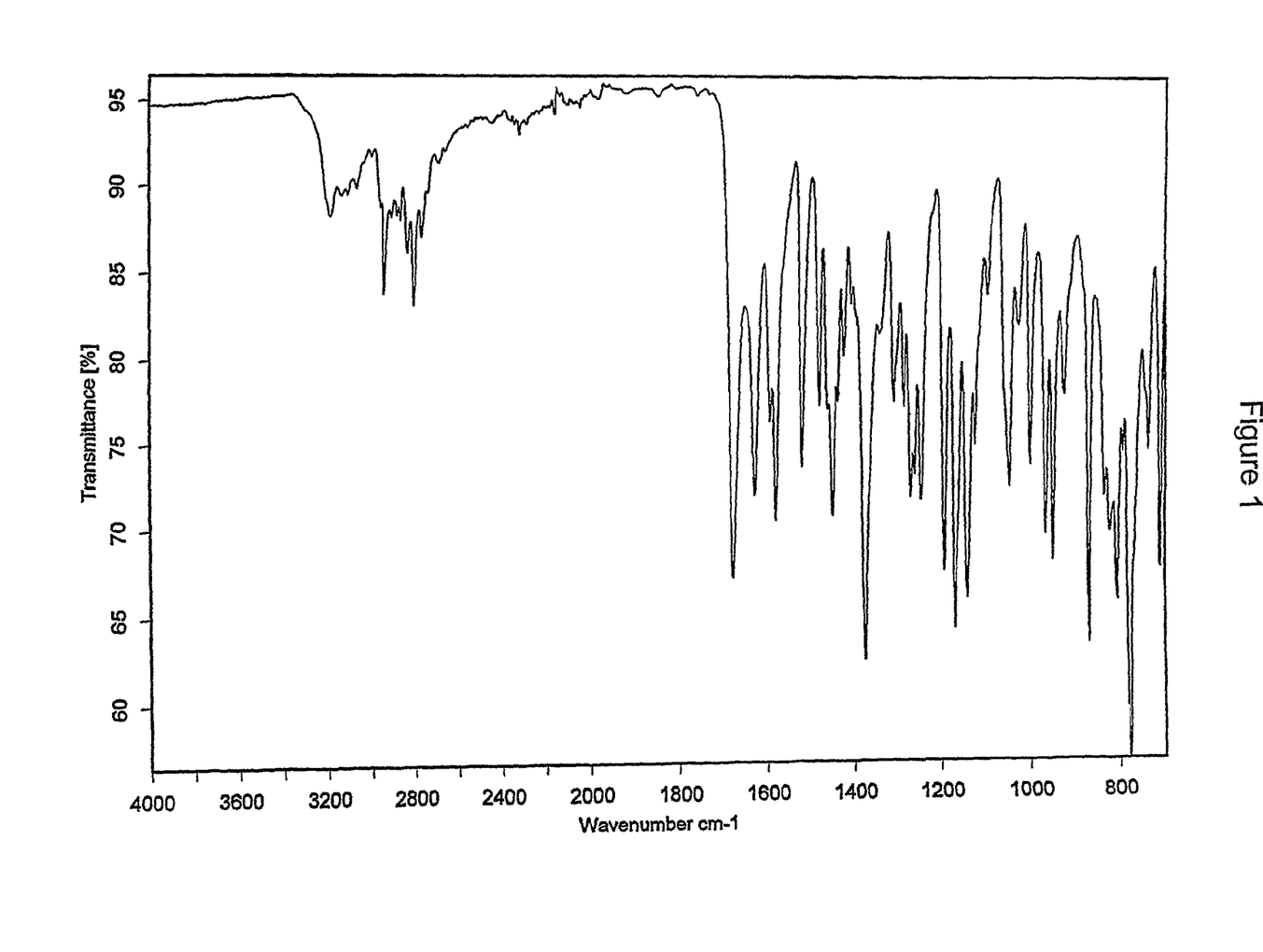
FIG. 1: Infrared spectrum of form X of aripiprazole.

Form X of aripiprazole may be also characterized by a typical infrared spectrum as shown in FIG. 1. Accordingly, in a further preferred embodiment, the present invention relates to form X of aripiprazole characterized by an infrared spectrum substantially in accordance with FIG. 1. Characteristic bands are present at 2939, 2803, 1677, 1374, 1191, 1168, 1045, 868, 822 and 736 cm$^{-1}$.

Figure 7:
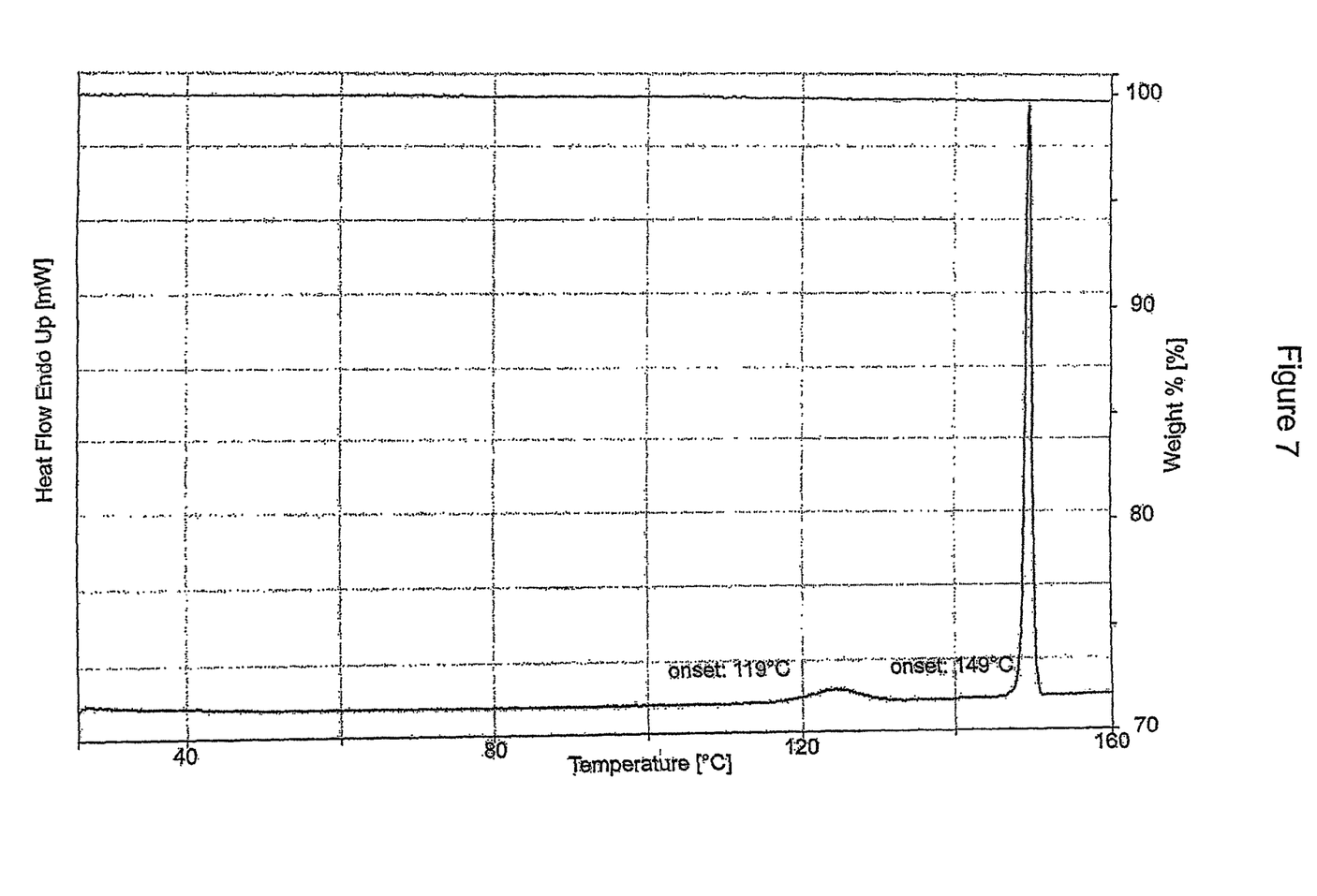
FIG. 7: Thermogravimetric and differential scanning calorimetric curve of form X of aripiprazole.

In addition, form X of aripiprazole shows a typical DSC curve at a heating rate of 5° K/min and practically no mass loss in the TGA analysis. Typical thermograms of form X of aripiprazole are shown in FIG. 7. It can be seen that the DSC curve of form X shows two specific endothermic peaks with onset temperatures of about 119° C. and 149° C.

Accordingly, in a further preferred embodiment, the present invention relates to form X of aripiprazole characterized by two endothermic peaks with onset temperatures of about 119° C. and 149° C. at a heating rate of 5K/min in differential scanning calorimetry.

Figure 10:
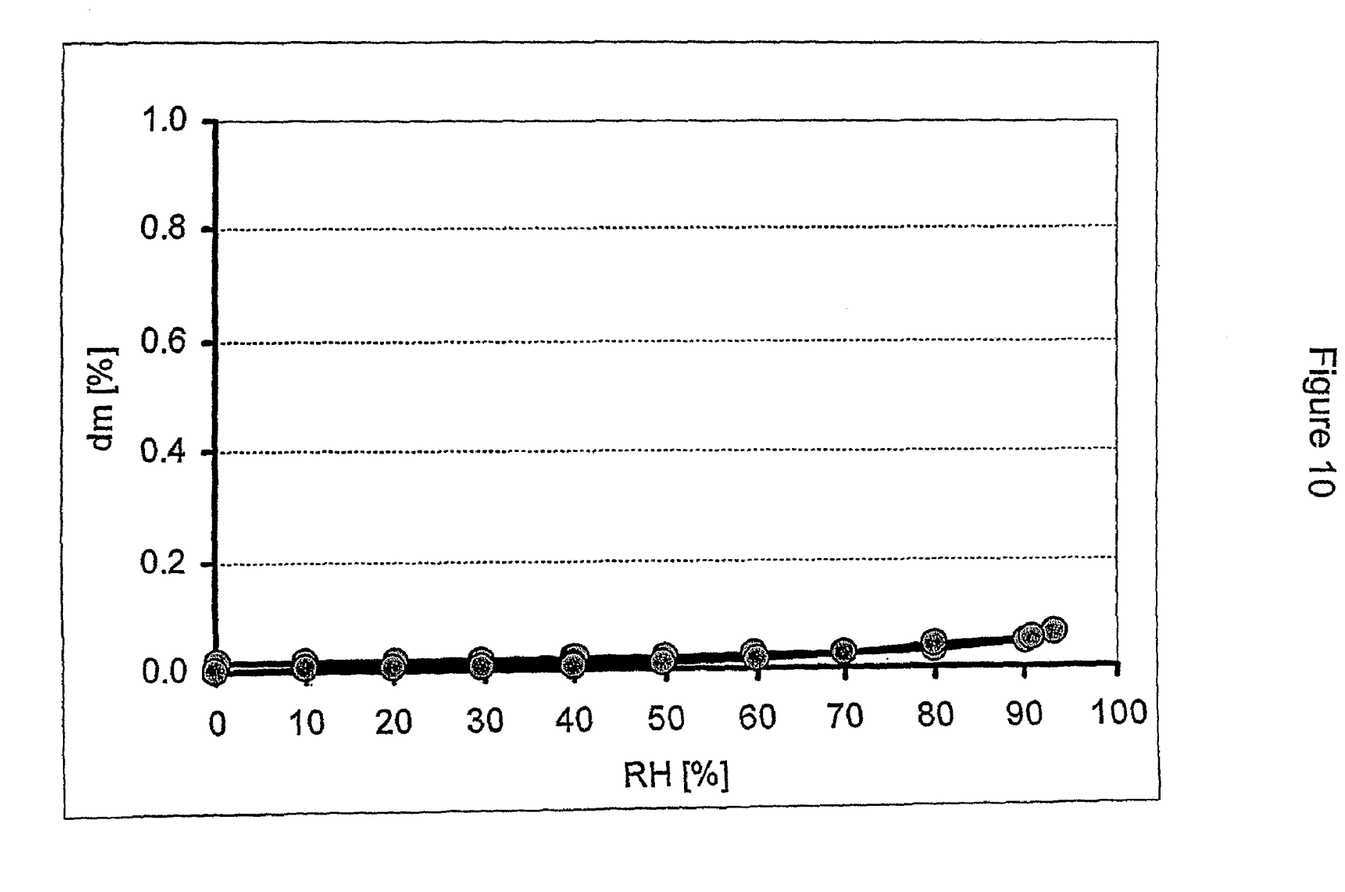
FIG. 10: Moisture sorption isotherm of form X of aripiprazole.

Form X of aripiprazole is a novel anhydrous form, hereinafter also referred to as "form X", which is particularly stable and hence is suitable for bulk preparation and handling. Form X of aripiprazole has been found to be of low hygroscopicity and does not substantially convert into a hydrated form of aripiprazole. This can be seen from the moisture sorption isotherm of form X which is shown in FIG. 10.

The present invention further relates to aripiprazole ethanol hemisolvate characterized by an X-ray powder diffraction pattern with peaks at 17.4, 18.1, 19.6, 23.3 and 27.9 degrees 2θ.

Figure 5:
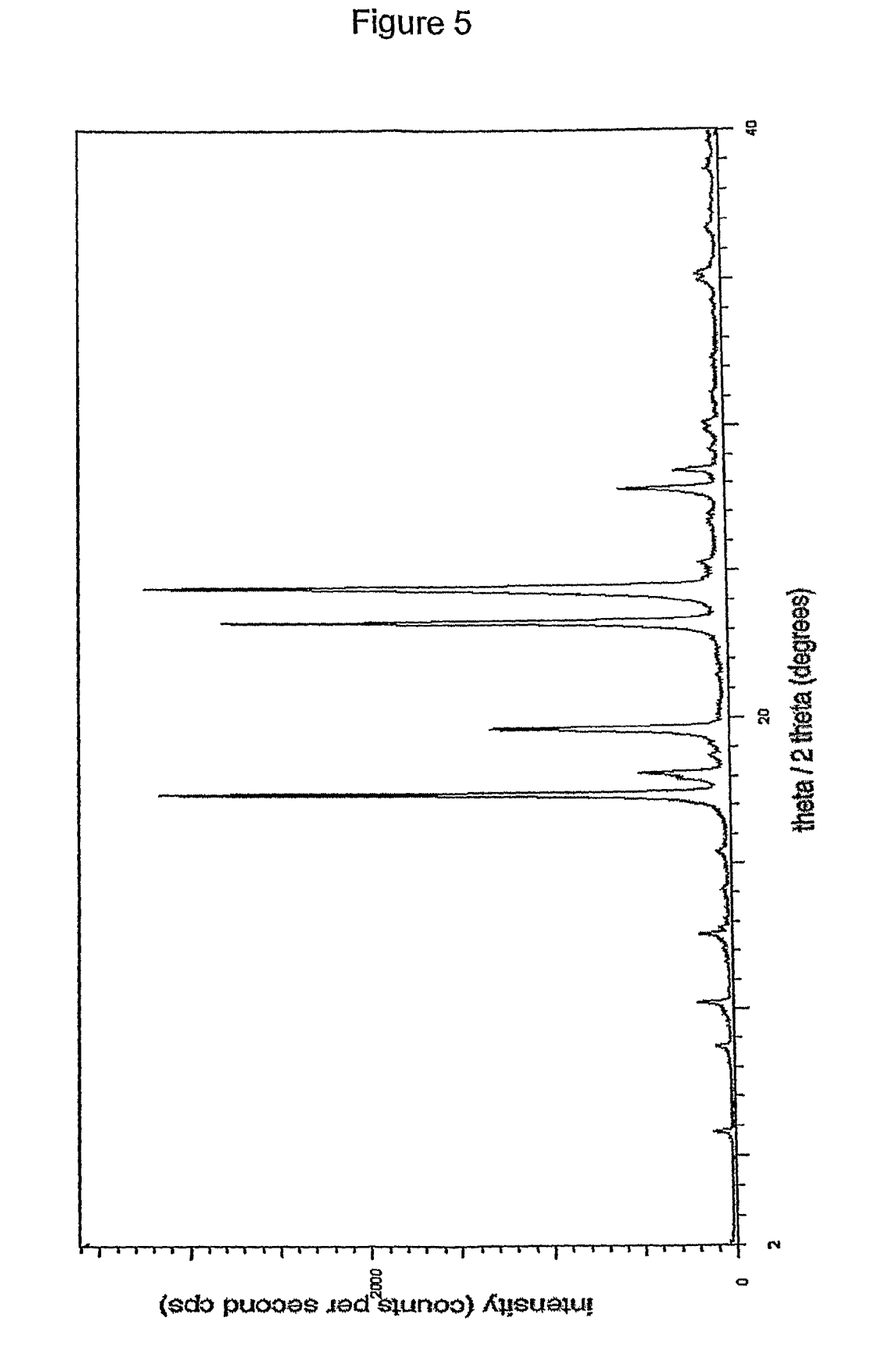
FIG. 5: X-ray powder diffraction pattern of aripiprazole ethanol hemisolvate.

A characteristic X-ray powder diffraction pattern of aripiprazole ethanol hemisolvate is shown in FIG. 5 and some characteristic peaks are listed in Table 2. Accordingly, in a preferred embodiment, the present invention relates to aripiprazole ethanol hemisolvate characterized by an X-ray powder diffraction pattern substantially in accordance with Table 2 and FIG. 5.

Figure 2:
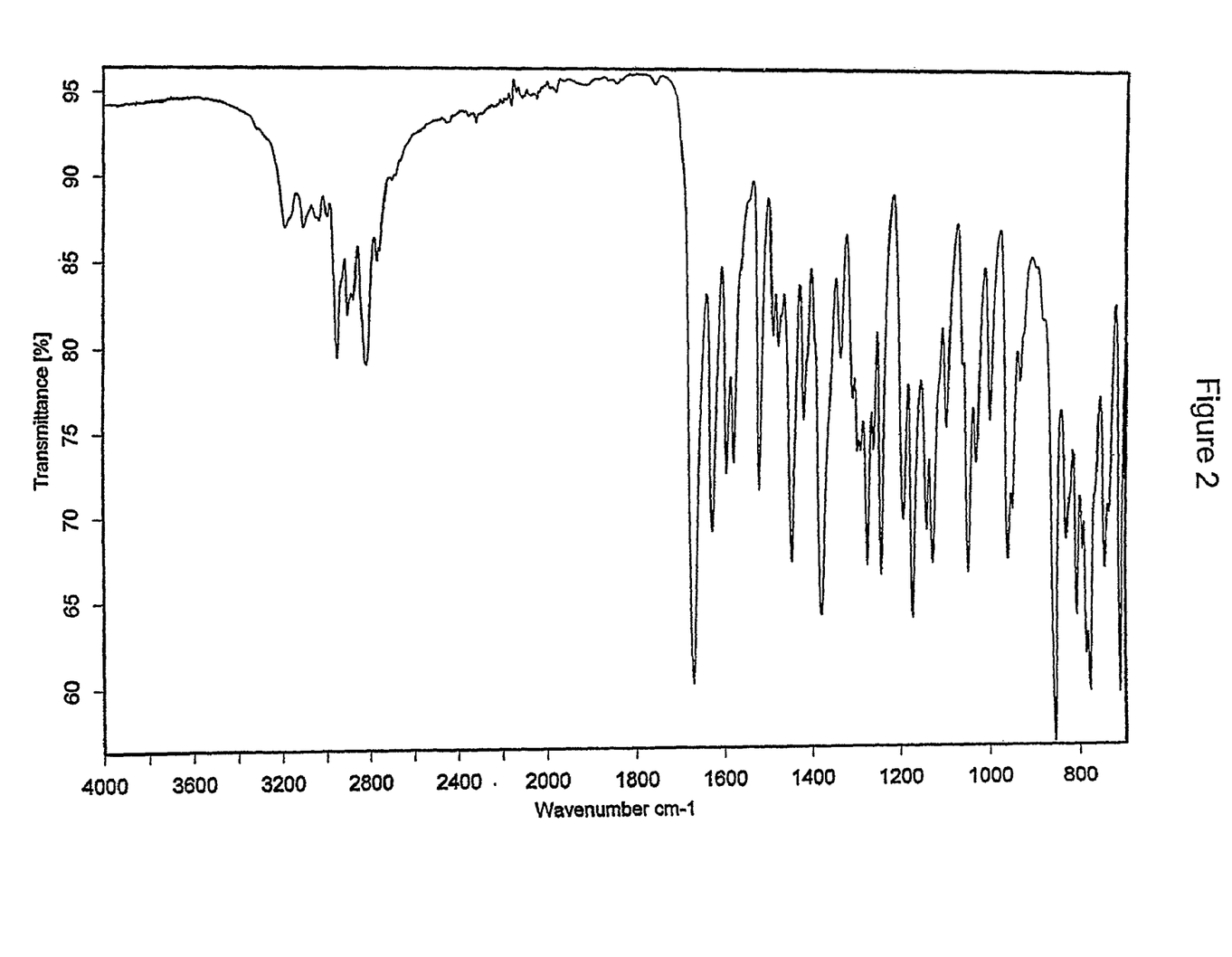
FIG. 2: Infrared spectrum of aripiprazole ethanol hemisolvate.

Aripiprazole ethanol hemisolvate may be also characterized by a typical infrared spectrum as shown in FIG. 2. Accordingly, in a further preferred embodiment, the present invention relates to aripiprazole ethanol hemisolvate characterized by an infrared spectrum substantially in accordance with FIG. 2. Characteristic bands are present at 2949, 2816, 1670, 1378, 1192, 1171, 1047, 854, 830 and 746 cm$^{-1}$.

Figure 8:
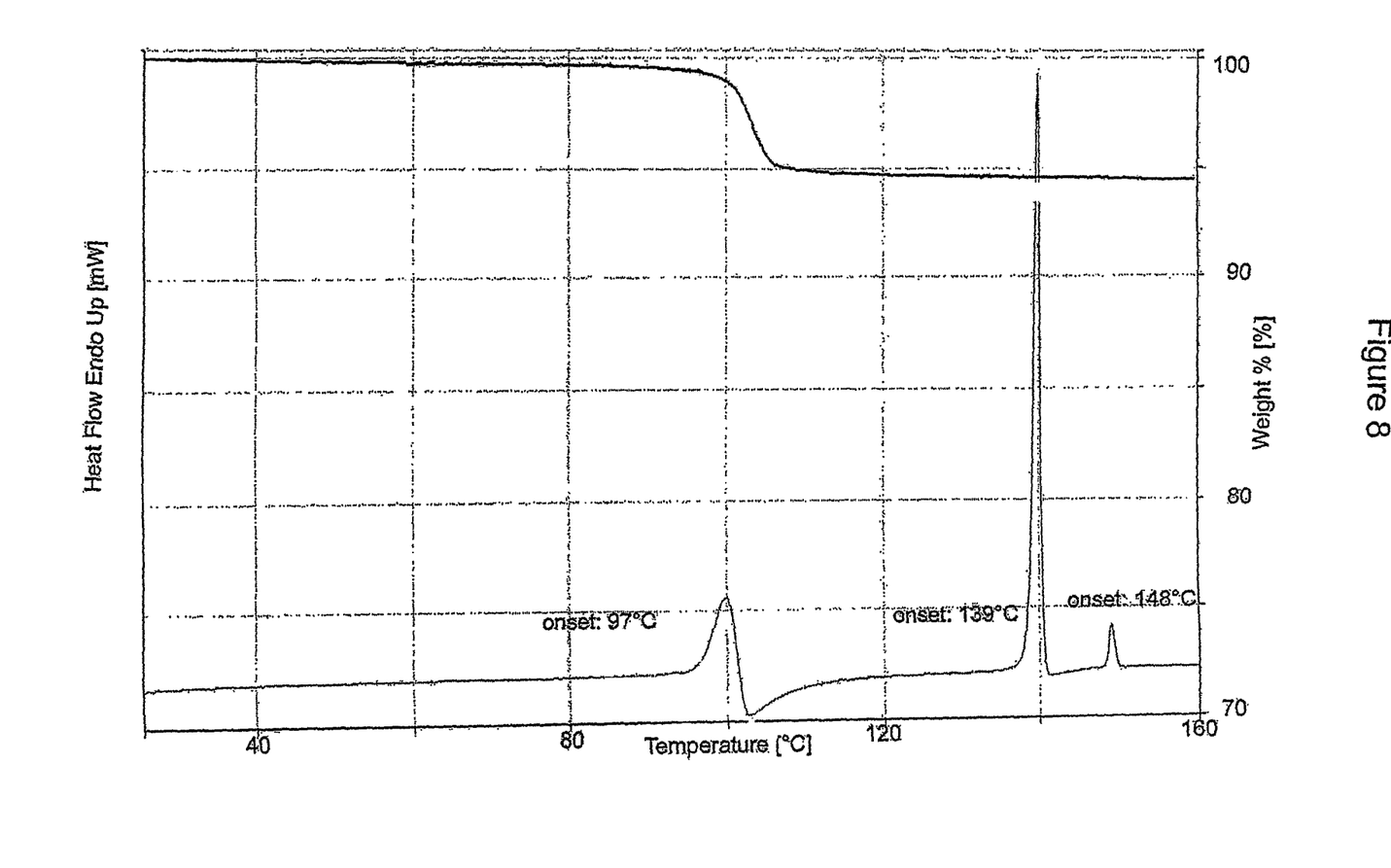
FIG. 8: Thermogravimetric and differential scanning calorimetric curve of aripiprazole ethanol hemisolvate.

In addition, aripiprazole ethanol hemisolvate shows a typical step in the TGA curve and a characteristic DSC curve at a heating rate of 5° K/min. Typical thermograms of aripiprazole ethanol hemisolvate are shown in FIG. 8. It can be seen that the DSC curve of aripiprazole ethanol hemisolvate (sample pan with pinhole) shows an endothermic peak with an onset temperature of about 97° C. followed by an exothermic event and two endothermic peaks with onset temperatures of about 139° C. and 148° C.

Accordingly, in a further preferred embodiment, the present invention relates to aripiprazole ethanol hemisolvate characterized by an endothermic peak with an onset temperature of about 97° C. followed by an exothermic event and two endothermic peaks with onset temperatures of about 139° C. and 148° C. at a heating rate of 5° K/min in differential scanning calorimetry.

In another aspect, the present invention relates to aripiprazole methanol solvate characterized by an X-ray powder diffraction pattern with peaks at 11.5, 17.3, 18.5, 19.8, 23.1, 24.4 and 26.9 degrees 2θ.

Figure 3:
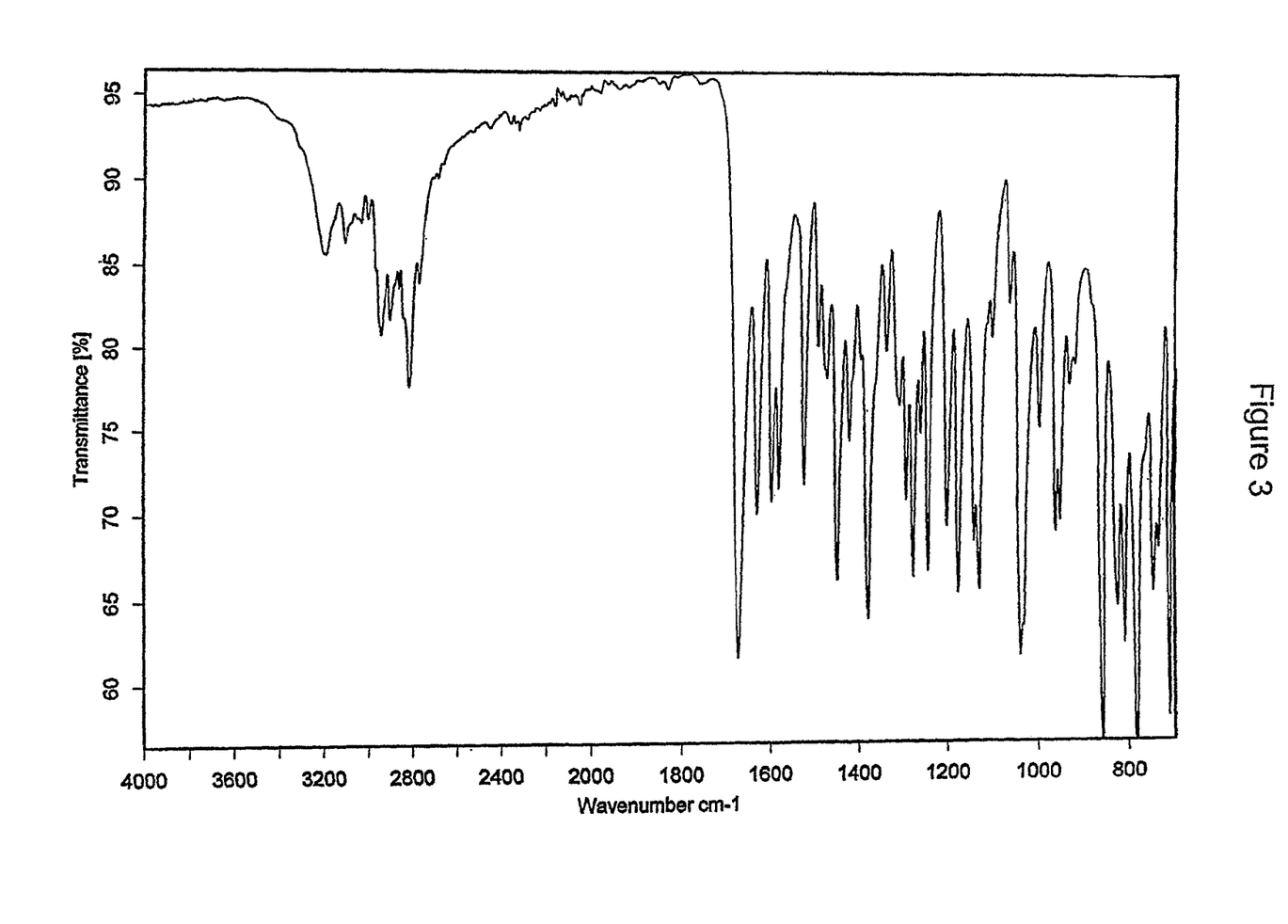
FIG. 3: Infrared spectrum of aripiprazole methanol solvate.
Figure 6:
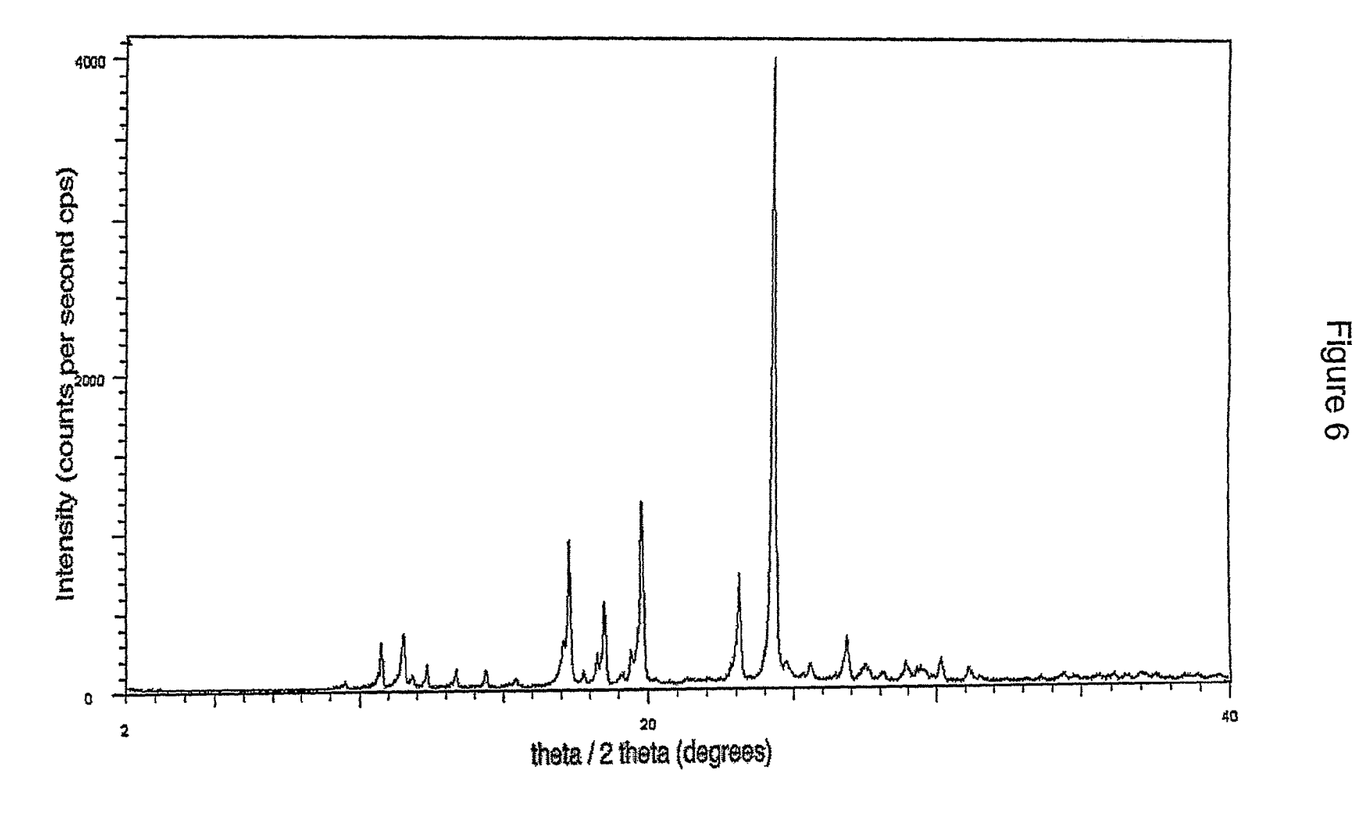
FIG. 6: X-ray powder diffraction pattern of aripiprazole methanol solvate.

A characteristic X-ray powder diffraction pattern of aripiprazole methanol solvate is shown in FIG. 6 and some characteristic peaks are listed in Table 3. Accordingly, in a preferred embodiment, the present invention relates to aripiprazole methanol solvate characterized by an X-ray powder diffraction pattern substantially in accordance with Table 3 and FIG. 6. Aripiprazole methanol solvate may be also characterized by a typical infrared spectrum as shown in FIG. 3. Accordingly, in a further preferred embodiment, the present invention relates to aripiprazole methanol solvate characterized by an infrared spectrum substantially in accordance with FIG. 3. Characteristic bands are present at 2942, 2814, 1671, 1377, 1199, 1174, 1037, 857, 824 and 746 cm$^{-1}$.

Figure 9:
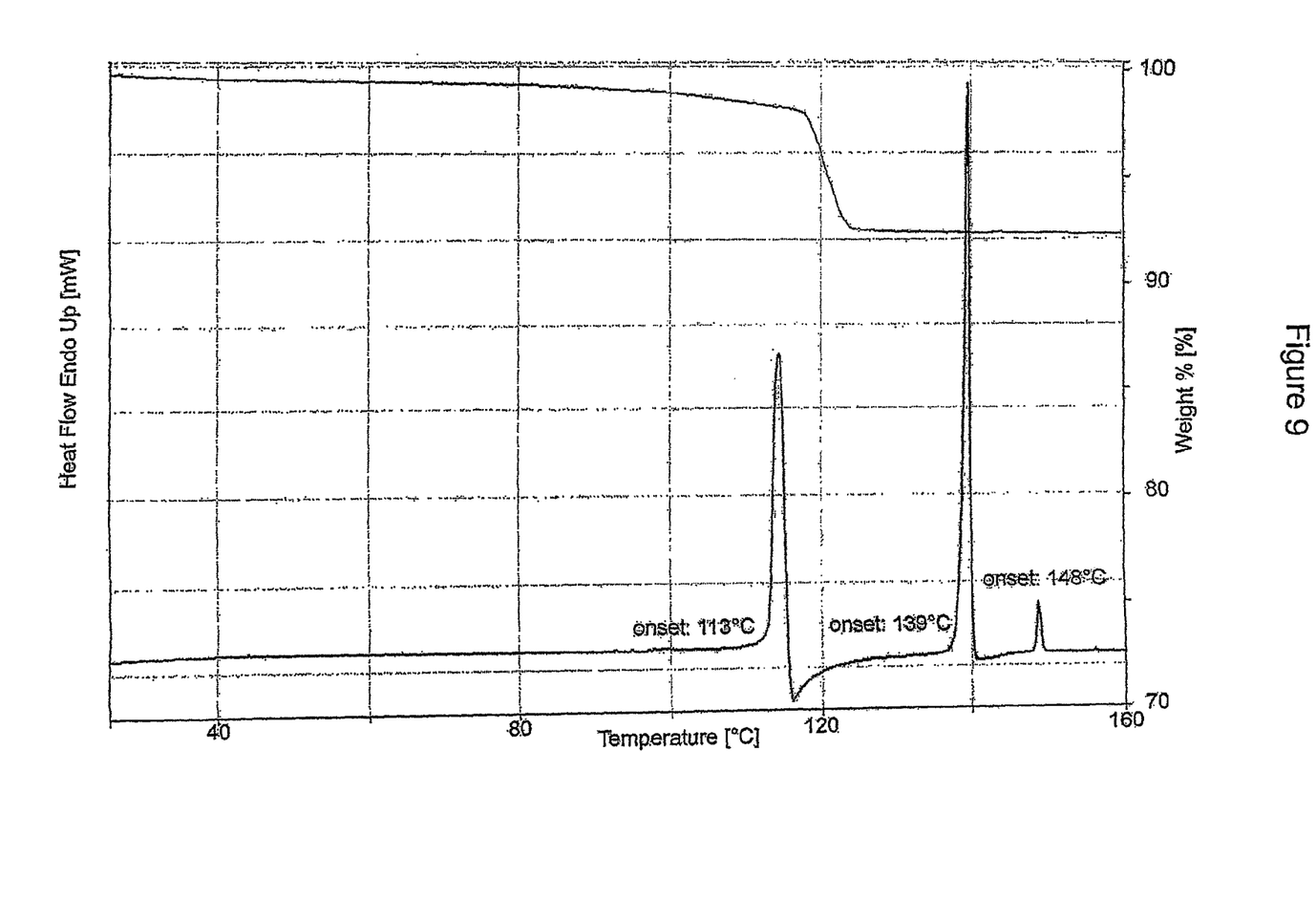
FIG. 9: Thermogravimetric and differential scanning calorimetric curve of aripiprazole methanol solvate.

In addition, aripiprazole methanol solvate shows a typical step in the TGA curve and a characteristic DSC curve at a heating rate of 5° K/min. Typical thermograms of aripiprazole methanol solvate are shown in FIG. 9. It can be seen that the DSC curve of aripiprazole methanol solvate (sample pan with pinhole) shows an endothermic peak with an onset temperature of about 113° C. followed by an exothermic event and two endothermic peaks with onset temperatures of about 139° C. and 148° C.

Accordingly, in a further preferred embodiment, the present invention relates to aripiprazole methanol solvate characterized by an endothermic peak with an onset temperature of about 113° C. followed by an exothermic event and two endothermic peaks with onset temperatures of about 139° C. and 148° C. at a heating rate of 5° K/min in differential scanning calorimetry.

As said before, each of the above mentioned data alone are sufficient to characterize each of the new polymorphs of aripiprazole. Therefore, further embodiments of the present invention relate to each polymorph being characterized by its typical X-ray powder diffraction pattern or its typical infrared spectrum or its typical thermogravimetric/differential scanning calorimetric curve.

In one embodiment, the present invention provides a first process for preparing form X of aripiprazole, comprising the steps of:
a) dissolving aripiprazole in a suitable solvent by heating
b) slowly cooling the solution to room temperature or below to effect crystallization
c) optionally isolating crystalline form X of aripiprazole.

For preparing form X of aripiprazole according to the above first process, any other form of aripiprazole may be used, e.g. the forms disclosed in WO 03/026659 (conventional hydrate, hydrate A, conventional anhydride, anhydrate B, anhydrate C, anhydrate D, anhydrate E, anhydrate F, anhydrate G). In addition, also non-crystalline forms of aripiprazole such as the amorphous form and forms of low crystalline order or crude aripiprazole may be used.

In particular, the other novel forms of aripiprazole of the present invention described above, i.e. aripiprazole ethanol hemisolvate and aripiprazole methanol solvate or an aripiprazole hydrate may be used to prepare form X of aripiprazole. Of course, also mixtures of two or more different forms of aripiprazole may be used. Therefore, in a preferred embodiment, the form used in the above first process in step a) is aripiprazole ethanol hemisolvate and/or aripiprazole methanol solvate and/or aripiprazole hydrate.

According to the above first process a suitable solvent is a solvent in which the substance is not highly soluble. Unsuitable solvents are pure water, ethanol or methanol because the corresponding solvate is formed. In a preferred embodiment, the solvent used in step a) of the above first process is acetone, tetrahydrofuran or 2-propanol. The even more preferred solvent is 2-propanol.

The heating temperature applied in order to dissolve aripiprazole depends on the boiling point of the solvent used but usually will be in the range of 50° C. to 100° C. A preferred temperature is the boiling temperature of the solvent. If 2-propanol is used, the aripiprazole is dissolved preferably in a concentration of about 20 g to about 40 g per liter 2-propanol by heating, most preferably in a concentration of about 30 g to about 35 g aripiprazole per liter 2-propanol.

The crystallization step b) of the above first process may be facilitated by adding seed crystals of form X of aripiprazole. Accordingly, in a preferred embodiment, in the above first process in step b) seed crystals of form X of aripiprazole are added. In a preferred embodiment seeds are added to a solution of aripiprazole in 2-propanol at a temperature of between approximately 80° C. to 40° C., preferably at a temperature of about 70° C. to 50° C., preferably at a temperature of about 70° C. to 60° C. and the suspension is then cooled slowly to a temperature of about 60° C. to 40° C. preferably to a temperature of about 50° C. to 40° C. in a first step followed by further cooling of the suspension to about 20° C. to 0° C., preferably 10° C. to 0° C. in a second step. Optionally the suspension is heated again to a temperature of 40° C. to 60° C., preferably to a temperature of about 50° C. to 60° C. and cooled again as described above.

In another embodiment, the present invention provides a second process for preparing form X of aripiprazole characterized in that a suspension of aripiprazole in a suitable solvent is seeded with crystals of form X and the suspension is stirred at a suitable temperature in order to effect transformation of the used form of aripiprazole into form X.

Just as for the first process described above also for this second process for preparing form X of aripiprazole any other form of aripiprazole, i.e. any crystalline unsolvated or solvated form, non-crystalline or amorphous form or crude aripiprazole may be used. Preferably, the other novel forms of aripiprazole of the present invention, i.e. aripiprazole ethanol hemisolvate and aripiprazole methanol solvate or an aripiprazole hydrate may be used.

However, this second process is based on the solution mediated transformation of any form of aripiprazole which is thermodynamically less stable under given conditions than form X. Therefore, the transformation into form X is a thermodynamically controlled process due to the fact that form X has the lowest Gibbs free energy at temperatures at and below about 60° C. Consequently, all known solid crystalline or non-crystalline forms, of aripiprazole may be used in the present process.

According to the above second process a suitable solvent is a solvent or solvent mixture which does not form a crystalline solvate with aripiprazole and in which the substance is not highly soluble. In a preferred embodiment, the solvent used in the above second process for preparing form X of aripiprazole is selected from 2-propanol, acetone, 1-butanol or 1-propanol.

The temperature at which the suspension is stirred in order to effect transformation of the suspended form of aripiprazole into form X depends on the form of aripiprazole and the solvent used. Room temperature or an elevated temperature may be applied but usually it will be in the range of 10° C. to 60° C. However, it is crucial that solvent and temperature are chosen such that the used form of aripiprazole remains in the condition of a suspension and does not become dissolved. It is well within the general knowledge of a person skilled in the art to determine a suitable solvent and temperature accordingly.

In a preferred embodiment the solvent is 2-propanol and the preferred temperature range is about 10° C. to about 80° C., preferably at a temperature of about 60° C. to about 40° C., most preferable at a temperature of about 60° C. to about 50° C. for a time to form form X of aripiprazole. Aripiprazole is then isolated after cooling the solution. A time sufficient for the formation of form X varies from a view minutes, e.g. 15 to 30 min to several days, e.g. 2 to 6 days. Optionally in intervals the suspension may be cooled to a lower temperature, e.g. to a temperature to about ambient temperature and the suspension is then reheated to the desired temperature.

In a further embodiment, the present invention provides a first process for preparing aripiprazole ethanol hemisolvate, comprising the steps of:
a) dissolving aripiprazole in ethanol by heating
b) slowly cooling the solution to room temperature or below to effect crystallization
c) isolating the crystalline ethanol hemisolvate
d) drying the ethanol hemisolvate at a temperature below about 60° C.

Just as for the processes for preparing form X of aripiprazole described above also for this first process for preparing aripiprazole ethanol hemisolvate any other form of aripiprazole, i.e. any crystalline unsolvated or solvated form, any non-crystalline or amorphous form and crude aripiprazole may be used. Preferably, the other novel forms of aripiprazole of the present invention, i.e. form X of aripiprazole and aripiprazole methanol solvate or an aripiprazole hydrate may be used.

The heating temperature applied in order to dissolve aripiprazole depends on the boiling point of the solvent used but usually will be in the range of 50° C. to 100° C. A preferred temperature is the boiling temperature of the solvent.

Drying the ethanol hemisolvate at a temperature below about 60° C. may be performed in different ways under different suitable conditions. Drying time and drying temperature are inversely related, so that for example the drying time will be longer the lower the drying temperature, and shorter the higher the drying temperature. Particularly suitable and preferred are air drying at room temperature, drying under vacuum at room temperature over night or drying at 50° C. for 2 hours.

Alternatively, instead of using pure ethanol as solvent for preparing the ethanol hemisolvate, aripiprazole may be dissolved in a solvent in which aripiprazole is soluble at room temperature such as e.g. methylene chloride, tetrahydrofuran or amides like e.g. dimethylformamide, dimethylacetamide or N-methylpyrrolidone. A suitable solvent is a solvent which allows dissolving one gram aripiprazole in a volume of approximately 10 ml solvent or less at room temperature. Due to the good solubility only a little quantity of the solvent is needed. The concentrated solution is then diluted with ethanol resulting in the crystallization of aripiprazole ethanol hemisolvate.

This process provides high yields of aripiprazole ethanol hemisolvate and also represents a practical method for purification of crude aripiprazole, because most of the impurities of crude aripiprazole are more soluble than aripiprazole ethanol hemisolvate and remain in solution.

Accordingly, in a further embodiment, the present invention provides a second process for preparing aripiprazole ethanol hemisolvate, comprising the steps of:
a) dissolving aripiprazole in a solvent in which aripiprazole is soluble at room temperature
b) diluting the solution with ethanol
c) isolating the crystalline ethanol hemisolvate
d) drying the ethanol hemisolvate at a temperature below about 60° C.

In a preferred embodiment, the solvent used in the above second process for preparing aripiprazole ethanol hemisolvate is selected from methylene chloride, tetrahydrofuran, dimethylformamide, dimethylacetamide or N-methylpyrrolidone.

With respect to the aripiprazole form used in step a) and the performance of drying step d) the same applies as said above for the first process for preparing aripiprazole ethanol hemisolvate.

In a further embodiment, the present invention provides a third process for preparing aripiprazole ethanol hemisolvate characterized in that a suspension of aripiprazole in ethanol is stirred at a suitable temperature in order to effect transformation of the used form of aripiprazole into aripiprazole ethanol hemisolvate.

With respect to the aripiprazole form used the same applies as said above for the first and second process for preparing aripiprazole ethanol hemisolvate.

The temperature at which the suspension is stirred in order to effect transformation of the suspended form of aripiprazole into aripiprazole ethanol hemisolvate may be room temperature or an elevated temperature. Usually, it will be in the range of 10° C. to 40° C. However, it is crucial that the temperature is chosen such that the used form of aripiprazole remains in the condition of a suspension and does not become dissolved. It is well within the general knowledge of a person skilled in the art to determine a suitable temperature accordingly.

The present invention also relates to a first process for preparing aripiprazole methanol solvate comprising the steps of:
a) dissolving aripiprazole in methanol by heating
b) slowly cooling the solution to room temperature or below to effect crystallization
c) isolating the crystalline methanol solvate
d) drying the methanol solvate at a temperature below about 60° C.

Also for this first process for preparing aripiprazole methanol solvate any form of aripiprazole, i.e. any crystalline unsolvated or solvated form, any non-crystalline or amorphous form and crude aripiprazole may be used. Preferably, the other novel forms of aripiprazole of the present invention, i.e. form X of aripiprazole and aripiprazole ethanol hemisolvate or an aripiprazole hydrate may be used.

Drying the methanol solvate at a temperature below about 60° C. may be performed in different ways under different suitable conditions. Drying time and drying temperature are inversely related, so that for example the drying time will be longer the lower the drying temperature, and shorter the higher the drying temperature. Particularly suitable and preferred are air drying at room temperature, drying under vacuum at room temperature over night or drying at 50° C. for 2 hours.

Alternatively, instead of using pure methanol as solvent for preparing the methanol solvate, aripiprazole may be dissolved in a solvent in which aripiprazole is soluble at room temperature such as e.g. methylene chloride, tetrahydrofuran or amides like e.g. dimethylformamide, dimethylacetamide or N-methylpyrrolidone. A suitable solvent is a solvent which allows dissolving one gram aripiprazole in a volume of approximately 10 milliliters solvent or less at room temperature. Due to the good solubility only a little quantity of the solvent is needed. The concentrated solution is then diluted with methanol resulting in the crystallization of aripiprazole methanol solvate.

This process provides high yields of aripiprazole methanol solvate and also represents a practical method for purification of crude aripiprazole, because most of the impurities of crude aripiprazole are more soluble than aripiprazole methanol solvate and remain in solution.

Accordingly, in another aspect, the present invention relates to a second process for preparing aripiprazole methanol solvate, comprising the steps of:
a) dissolving aripiprazole in a solvent in which aripiprazole is soluble at room temperature
b) diluting the solution with methanol
c) isolating the crystalline methanol solvate
d) drying the methanol solvate at a temperature below about 60° C.

In a preferred embodiment, the solvent used in the above second process for preparing aripiprazole methanol solvate is selected from methylene chloride, tetrahydrofuran, dimethylformamide, dimethylacetamide or N-methylpyrrolidone.

With respect to the aripiprazole form used in step a) and the performance of drying step d) the same applies as said above for the first process for preparing aripiprazole methanol solvate.

In a further embodiment, the present invention provides a third process for preparing aripiprazole methanol solvate characterized in that a suspension of aripiprazole in methanol is stirred at a suitable temperature in order to effect transformation of the used form of aripiprazole into aripiprazole methanol solvate.

With respect to the aripiprazole form used the same applies as said above for the first and second process for preparing aripiprazole methanol solvate.

The temperature at which the suspension is stirred in order to effect transformation of the suspended form of aripiprazole into aripiprazole methanol solvate may be room temperature or an elevated temperature. Usually, it will be in the range of 10° C. to 40° C. However, it is crucial that the temperature is chosen such that the used form of aripiprazole remains in the condition of a suspension and does not become dissolved. It is well within the general knowledge of a person skilled in the art to determine a suitable temperature accordingly.

The novel forms of aripiprazole of the present invention may be used alone as antipsychotic drugs or in the form of a suitable pharmaceutical composition containing the novel form together with one or more suitable pharmaceutically acceptable carriers. The pharmaceutical compositions containing the novel forms of aripiprazole of the present invention are prepared according to known processes.

Accordingly, the present invention relates to form X of aripiprazole or aripiprazole ethanol hemisolvate for use as a medicament.

The novel forms of aripiprazole are particularly useful for the treatment of schizophrenia. Therefore, the present invention also relates to the use of form X of aripiprazole or aripiprazole ethanol hemisolvate for the preparation of a medicament for the treatment of schizophrenia.

The present invention further relates to a pharmaceutical composition comprising an effective amount of form X of aripiprazole or aripiprazole ethanol hemisolvate and a pharmaceutically acceptable carrier. The pharmaceutical composition may be prepared via a wet granulation process as known in the state of the art and as described for other crystalline and polymorphic forms in WO 03/026659. Another suitable preparation may be forming flash-melt tablets.

The invention is further described by reference to the following examples. These examples are provided for illustration purposes only and are not intended to be limiting the present invention in any way.

EXAMPLES

The infrared spectra are recorded using a BRUKER FTIR-Tensor 27 with diamond ATR. The XRPD is recorded on a AXS-BRUKER X-ray powder diffractometer D-8 using the following acquisition conditions: tube anode: Cu; generator tension: 40 kV; generator current: 40 mA; start angle: 2.0° θ; end angle: 40.0° θ; step size: 0.01° θ; time per step: 2 seconds. Differential scanning calorimetry (DSC) is performed with a DSC 7 (Perkin-Elmer, Norwalk, Conn., USA) using the Pyris 2.0 software. Samples are weighed into 25 µl Al-Pans. Dry nitrogen is used as the purge gas (purge: 20 ml min$^{-1}$).

Thermogravimetric analysis is performed with the Thermogravimetric-System TGA-7 using the Pyris-Software for Windows NT, (Perkin-Elmer, Norwalk, Conn., USA), 50 µl platin-pans, nitrogen purge gas (sample purge: 20 mL min$^{-1}$, balance purge: 40 mL min$^{-1}$).

Example 1

25 g of aripiprazole Anhydrate Form A obtained as described in EP 367141 B1 are stirred in 250 ml isopropanol and heated at boiling until a clear solution is obtained. After cooling to room temperature under stirring the precipitated product is filtered and dried at room temperature under vacuum over night to give 24.12 g (96.5%) of the anhydrous polymorph referred to herein as form X.

The form X crystals of aripiprazole anhydride obtained above provide an infrared spectrum with peaks at 2939, 2803, 1677, 1374, 1191, 1168, 1045, 868, 822 and 736 cm$^{-1}$ (FIG. 1). The XRPD pattern of form X of aripiprazole with characteristic XRPD angles, d-spacings and relative intensities is shown in Table 1 and in FIG. 4.

TABLE 1

X-Ray Powder Diffraction (XRPD) pattern of form X of aripiprazole. Values: Interplanar spacings (d, in Å, Angstroem), characteristic XRPD angles (in degrees 2-theta) and relative intensities (in %)

| ° Angle 2 theta | d-value (Å) | Rel. Intensity (%) |
|---|---|---|
| 5.3 | 16.56 | 7 |
| 10.0 | 8.88 | 22 |
| 10.7 | 8.24 | 7 |
| 11.1 | 7.99 | 8 |
| 11.6 | 7.64 | 22 |
| 12.6 | 7.04 | 10 |
| 15.7 | 5.66 | 23 |
| 16.3 | 5.45 | 41 |
| 18.5 | 4.79 | 21 |
| 18.9 | 4.69 | 8 |
| 19.8 | 4.48 | 14 |
| 20.0 | 4.43 | 12 |
| 20.4 | 4.34 | 20 |
| 21.8 | 4.08 | 39 |
| 22.2 | 4.00 | 100 |
| 23.3 | 3.81 | 24 |
| 24.4 | 3.64 | 9 |
| 26.0 | 3.42 | 13 |
| 27.0 | 3.29 | 9 |
| 28.8 | 3.10 | 13 |
| 33.6 | 2.66 | 6 |
| 35.3 | 2.54 | 7 |
| 35.6 | 2.52 | 6 |
| 39.4 | 2.29 | 6 |

Form X of aripiprazole shows a typical DSC curve at a heating rate of 5K/min and practically no mass loss in the TGA analysis. Typical thermograms of form X of aripiprazole are shown in FIG. 7. It can be seen that form X shows two specific endothermic peaks with onset temperatures of about 119° C. and 149° C.

Example 2

5 g of aripiprazole Anhydrate Form A obtained as described in EP 367141 B1 are stirred in 20 ml tetrahydrofuran and heated at boiling until a clear solution is obtained. After cooling to room temperature the suspension is stirred for additional three hours and then allowed to stand two days in a refrigerator. The precipitated product is filtered and dried at room temperature under vacuum over night to give 2.95 g (59%) of form X of the product.

Example 3

A suspension of 7 g of aripiprazole Anhydrate Form A obtained as described in reference example 1 of WO 03/026659 is stirred in 50 ml acetone and heated to reflux for 7.5 hours. The mixture is filtered and the insoluble solid dried in an desiccator at room temperature over night to yield 4.48 g (64%) of form X of the product.

Example 4

100 g crude aripiprazole prepared as described in EP 367141 B1 are suspended in 1500 ml absolute ethanol and then heated to reflux. The resulting solution is slowly cooled to room temperature to crystallize the product. After stirring at 0° C. for one hour the precipitated product is filtered and dried at room temperature under vacuum for 17 hours to give 102.7 g (97.7%) of the ethanol hemisolvate of the product. The crystals are colorless plate form. The content of ethanol in the product is about 5.0% by weight i.e. the compound is an ethanol hemisolvate containing half a mol of ethanol per mol aripiprazole.

The ethanol hemisolvate of aripiprazole obtained above provides an infrared spectrum with peaks at 2949, 2816, 1670, 1378, 1192, 1171, 1047, 854, 830 and 746 $cm^{-1}$ (FIG. 2). The XRPD pattern of aripiprazole ethanol hemisolvate with characteristic XRPD angles, d-spacings and relative intensities is shown in Table 2 and in FIG. 5.

TABLE 2

X-Ray Powder Diffraction (XRPD) pattern of aripiprazole ethanol hemisolvate. Values: Interplanar spacings (d, in Å, Angstroem), characteristic XRPD angles (in degrees 2-theta) and relative intensities (in %)

| ° Angle 2 theta | d-value (Å) | Rel. Intensity (%) |
|---|---|---|
| 5.8 | 15.28 | 3 |
| 8.6 | 10.22 | 2 |
| 10.2 | 8.70 | 4 |
| 12.5 | 7.05 | 4 |
| 15.4 | 5.75 | 2 |
| 16.7 | 5.31 | 3 |
| 17.4 | 5.09 | 55 |
| 18.1 | 4.90 | 8 |
| 18.7 | 4.74 | 3 |
| 19.6 | 4.52 | 22 |
| 23.3 | 3.82 | 36 |
| 24.5 | 3.64 | 100 |
| 25.3 | 3.52 | 3 |
| 27.9 | 3.20 | 9 |
| 28.5 | 3.13 | 3 |
| 35.0 | 2.56 | 3 |

Aripiprazole ethanol hemisolvate shows a typical endothermic curve in TGA and DSC analysis at a heating rate of 5° K/min. A typical thermogram of aripiprazole ethanol hemisolvate is shown in FIG. 8. It can be seen that aripiprazole ethanol hemisolvate shows an endothermic peak with an onset temperature of about 97° C. followed by an exothermic event and two endothermic peaks with onset temperatures of about 139° C. and 148.5° C.

Example 5

100 g crude aripiprazole prepared as described in EP 367141 B1 are suspended in 1500 ml absolute ethanol and then heated to reflux. The resulting solution is slowly cooled to room temperature to crystallize the product. After stirring at 0° C. for one hour the precipitated product is filtered and dried at 50° C. under vacuum for 2 hours.

Example 6

15 g of aripiprazole Anhydrate Form A obtained as described in EP 367141 B1 is added to 1600 ml methanol and the mixture is heated to reflux to get a clear solution. The solution is then slowly cooled to room temperature, stirred for another two hours and allowed to stand in a refrigerator for several days. The precipitated crystals are isolated by suction and dried at room temperature in vacuo to yield 15.2 g (93.7%) methanol solvate of the product. The crystals are colorless plate form. The content of methanol in the product is about 6.7% by weight i.e. the compound is a methanol monosolvate containing one mol of methanol per mol aripiprazole.

The methanol solvate of aripiprazole obtained above provides an infrared spectrum with peaks at 2942, 2814, 1671, 1377, 1199, 1174, 1037, 857, 824 and 746 $cm^{-1}$ (FIG. 3). The XRPD pattern of aripiprazole methanol solvate with characteristic XRPD angles, d-spacings and relative intensities is shown in Table 3 and in FIG. 6.

TABLE 3

X-Ray Powder Diffraction (XRPD) pattern of aripiprazole methanol solvate. Values: Interplanar spacings (d, in Å, Angstroem), characteristic XRPD angles (in degrees 2-theta) and relative intensities (in %)

| ° Angle 2 theta | d-value (Å) | Rel. Intensity (%) |
|---|---|---|
| 5.7 | 15.41 | <1 |
| 9.4 | 9.38 | 1 |
| 10.7 | 8.28 | 2 |
| 11.5 | 7.70 | 5 |
| 11.8 | 7.50 | 1 |
| 12.3 | 7.19 | 1 |
| 13.3 | 6.64 | 1 |
| 14.3 | 6.18 | 1 |
| 15.4 | 5.74 | 1 |
| 17.3 | 5.13 | 13 |
| 17.7 | 5.00 | 1 |
| 18.5 | 4.79 | 4 |
| 19.1 | 4.64 | 2 |
| 19.8 | 4.48 | 19 |
| 22.1 | 4.03 | 2 |
| 23.1 | 3.85 | 10 |
| 24.4 | 3.65 | 100 |
| 25.6 | 3.47 | 2 |
| 26.9 | 3.31 | 10 |
| 30.2 | 2.96 | 2 |
| 34.4 | 2.60 | 1 |

Aripiprazole methanol solvate shows a typical endothermic curve in TGA and DSC analysis at a heating rate of 5° K/min. A typical thermogram of aripiprazole methanol solvate is shown in FIG. 9. It can be seen that aripiprazole methanol solvate shows an endothermic peak with an onset temperature of about 113° C. followed by an exothermic event and two endothermic peaks with onset temperatures of about 139° C. and 148° C.

Example 7

1 g of crude aripiprazole Anhydrate Form A obtained as described in EP 367141 B1 is dissolved in 10 ml dichloromethane. The solution is diluted with 40 ml methanol and then allowed to stand in a refrigerator overnight. The precipitated crystals are isolated by suction and dried at room temperature in vacuo to yield 0.93 g (86.0%) methanol solvate of the product.

Example 8

5 g of the ethanol hemisolvate of example 4 are recrystallized from 55 ml isopropanol using seed crystals obtained in example 1 above. The yield is 4.5 g (94.6%) of form X of aripiprazole.

Example 9

Example 8 is repeated using 3 g of the methanol solvate obtained in example 5 above instead of the ethanol hemisolvate. The yield is 2.7 g (96.8%) of form X of aripiprazole.

Example 10

Example 8 is repeated but instead of using the ethanol hemisolvate as starting material 5 g of the aripiprazole hydrate obtained as described in reference example 3 of WO 03/026659 is used. The yield is 4.5 g (93.6%) of form X of aripiprazole.

Example 11

5 g of aripiprazole Anhydrate Form A obtained as described in EP 367141 B1 and 0.5 g of form X of aripiprazole are suspended in 55 ml isopropanol and heated at 50° C. overnight and then stirred at room temperature for four days. The unsoluble part of the reaction mixture is collected by filtration and dried in vacuo at room temperature over night to give 4.6 g (92%) of form X of aripiprazole.

Example 12

5 g of aripiprazole Anhydrate Form A obtained as described in EP 367141 B1 are suspended in 50 ml ethanol and stirred at room temperature for three hours. The solid is filtered and dried at room temperature under vacuum for 17 hours to give 5.0 g (95.1%) of the ethanol hemisolvate of aripiprazole.

Example 13

A suspension of 33 g of aripiprazole Anhydrate Form A obtained as described in EP 367141 B1 in 1000 ml of isopropanol is heated to reflux temperature. The resulting clear solution is cooled down to 65° C. under stirring and then seeded with 0.3 g of aripiprazole form X. After further cooling down to 60° C. a second portion of 0.3 g seeds of aripiprazole form X are added. The mixture is then slowly cooled down to 50° C. in one hour and then from 50° C. to 0° C. in one hour. After stirring at 0° C. for one hour, the obtained suspension is reheated to 50° C., stirred at this temperature for one or two hours, then again cooled to 0° C. After stirring for one hour the precipitated product is filtered and dried in vacuo at room temperature over night or at 60° C. for 3 hours to yield 31.8 g (94.5%) of form X of aripiprazole

Example 14

5 g aripiprazole hydrate obtained as described in example 22 are suspended in 80 ml isopropanol, seeded with 0.5 g aripiprazole form X and stirred at 50° C. over night. The suspension is cooled to room temperature, filtered and dried at room temperature under vacuum for 17 hours to give 4.61 g (85.5%) aripiprazole form X.

Example 15

Example 14 is repeated using 5 g of the ethanol hemisolvate as starting material instead of the hydrate. The yield is 4.51 g (84.3%) of form X of aripiprazole.

Example 16

2 g aripiprazole methanol solvate obtained as described in example 6 are suspended in 30 ml isopropanol, seeded with 0.5 g aripiprazole form X and stirred at 50° C. over night. The suspension is cooled to room temperature, filtered and dried at room temperature under vacuum for 17 hours to give 1.94 g (77.2%) aripiprazole form X.

The invention claimed is:

1. Process for preparing form X of aripiprazole, comprising the steps of:
   a) dissolving aripiprazole in a suitable solvent by heating
   b) slowly cooling the solution to room temperature or below to effect crystallization
   c) optionally isolating crystalline form X of aripiprazole.

2. Process according to claim 1, wherein the form of aripiprazole used in step a) is aripiprazole ethanol hemisolvate and/or aripiprazole methanol solvate and/or aripiprazole hydrate.

3. Process for preparing form X of aripiprazole according to claim 1 wherein the solvent in step a) is selected from the group consisting of acetone, tetrahydrofuran and 2-propanol and in step b) seed crystals of form X of aripiprazole are added.

4. Process according to claim 1, wherein the solvent is 2-propanol and the temperature range is about 40° C. to about 70° C.

5. Process for preparing form X of aripiprazole wherein a mixture of aripiprazole in a suitable solvent is seeded with crystals of form X aripiprazole and the mixture is stirred at a suitable temperature in order to effect transformation of the form of aripiprazole in the mixture into form X aripiprazole.

6. Process according to claim 5, wherein the solvent is selected from the group consisting of 2-propanol, acetone, 1-butanol and 1-propanol.

7. Process according to claim 5, wherein the solvent is 2-propanol and the temperature range is about 40° C. to about 60° C.

8. Process for preparing form X of aripiprazole, comprising the steps of:
   a) dissolving aripiprazole in a solvent medium which excludes pure water, ethanol, and methanol by heating the aripiprazole in the solvent medium to form a solution thereof
   b) cooling the solution to room temperature or below to effect crystallization
   c) isolating crystalline form X of aripiprazole from the solution.

9. Process for preparing form X of aripiprazole, comprising the steps of:
   a) dissolving aripiprazole in a solvent medium comprising a solvent selected from the group consisting of acetone, tetrahydrofuran and 2-propanol by heating the aripiprazole in the solvent medium to form a solution thereof
   b) cooling the solution to room temperature or below to cause formation of crystals therein containing substantially pure crystalline form X of aripiprazole, and c) isolating crystalline form X of aripiprazole from the solution.

10. Process for preparing form X aripiprazole according to claim 9 wherein the solvent excludes pure water, ethanol, and methanol.

11. Process for preparing form X aripiprazole according to claim 9 wherein seed crystals of form X of aripiprazole are added in association with step b).

12. Process for preparing form X aripiprazole according to claim 8 wherein the solvent medium comprises a solvent selected from the group consisting of acetone, tetrahydrofuran and 2-propanol.

13. Process for preparing form X aripiprazole according to claim 8 wherein the solution is cooled slowly in order to cause crystallization of aripiprazole form X from the solution.

* * * * *